United States Patent [19]

Kobayashi et al.

[11] Patent Number: 5,326,916
[45] Date of Patent: Jul. 5, 1994

[54] PROCESS FOR PRODUCING ACROLEIN

[75] Inventors: Yoshinori Kobayashi; Yasuo Matsumoto; Tadashi Mizuno; Masamitu Fukuda, all of Ehime, Japan

[73] Assignee: Sumitomo Chemical Co., Ltd., Osaka, Japan

[21] Appl. No.: 28,534

[22] Filed: Mar. 8, 1993

[30] Foreign Application Priority Data

Mar. 6, 1992 [JP] Japan .................. 4-049359

[51] Int. Cl.$^5$ .................. C07C 45/78; C07C 45/80
[52] U.S. Cl. .................. 568/492; 568/476; 568/479
[58] Field of Search .................. 568/476, 479, 492

[56] References Cited

U.S. PATENT DOCUMENTS

| | | | |
|---|---|---|---|
| 3,162,514 | 12/1964 | Roelen et al. | 568/492 |
| 3,218,357 | 11/1965 | Roelen et al. | 568/492 |
| 3,433,840 | 3/1969 | Shima et al. | 568/492 |
| 3,868,417 | 2/1975 | Duembgen et al. | 260/526 N |

FOREIGN PATENT DOCUMENTS

| | | | |
|---|---|---|---|
| 1199432 | 7/1970 | European Pat. Off. | C07C 57/04 |
| 0297788 | 1/1989 | European Pat. Off. | |
| 0001296 | 1/1981 | Japan | 568/492 |
| 2004886 | 4/1979 | United Kingdom | |

*Primary Examiner*—Werren B. Lone
*Attorney, Agent, or Firm*—Sughrue, Mion, Zinn, Macpeak & Seas

[57] ABSTRACT

A process for producing acrolein which comprises bringing a reaction gas resulting from a catalytic oxidation of propylene into contact in a cooling tower with a condensate which is being circulated through the cooling tower and a circulating part, thereby to cool and separate the reaction gas and discharge an effluent gas from the cooling tower, the condensate in a bottom part of the cooling tower having a temperature of from 35° to 50° C., the effluent gas discharged from the cooling tower having a temperature of from 35° to 55° C., the temperature of the effluent gas being kept nearly equal to or higher than the temperature of the condensate in the bottom part of the cooling tower, and a process for producing acrolein which comprises bringing a reaction gas resulting from the catalytic oxidation of propylene into contact in a cooling tower with a condensate which is being circulated through the cooling tower and a circulating part, thereby to cool and separate the reaction gases, the period of the residence time of the condensate in the cooling tower and the circulating part being from 0.5 to 3 hours.

5 Claims, 1 Drawing Sheet

PROCESS FOR PRODUCING ACROLEIN

FIELD OF THE INVENTION

The present invention relates to a process for producing acrolein by the catalytic oxidation of propylene. More particularly, the present invention relates to a method of inhibiting the formation of acrolein hydrate in a condensate when a reaction gas containing acrolein, acrylic acid, water, unreacted raw material gases, etc. is cooled to separate the acrolein.

BACKGROUND OF THE INVENTION

In a process for producing acrolein, a gas produced by a reaction of forming acrolein (hereinafter referred to as "reaction gas") containing acrolein, acrylic acid, water and others is generally sufficiently cooled by direct contact with a condensate in a packed tower or the like thereby to condense the acrylic acid, water and others, subsequently the acrolein remaining in the resulting gas phase is separated from the nitrogen and other gases by being absorbed in water or the like, and the absorbed acrolein is then stripped. Thus, high-purity acrolein is recovered.

The condensate contains acrolein and acrylic acid each in an amount of several percents by weight and further contains about 1% by weight of acrolein hydrate (hydroxypropionaldehyde). Since discarding the condensate necessitates costly wastewater treatment and results in deteriorated unit requirement of propylene, the acrolein and acrylic acid are usually recovered from the condensate. In order to recover the acrolein, the condensate is heated to strip the acrolein, which is then recovered along with the gas-phase acrolein described above. The remaining acrylic acid is recovered by extracting with a solvent and then separating from the solvent by distillation.

If the condensate, from which acrylic acid is to be recovered, contains an acrolein hydrate (hydroxypropionaldehyde) in a large amount, acrolein comes into the recovered acrylic acid to lower the purity of the acrylic acid.

Although the acrolein hydrate can be decomposed by elevating the temperature, this method is not preferred in that such high temperatures result in sludge formation and necessitate removal thereof.

SUMMARY OF THE INVENTION

An object of the present invention to provide a process for efficiently producing acrolein in which the formation of acrolein hydrate is inhibited in the condensate obtained by cooling a reaction gas resulting from the catalytic oxidation of propylene, to thereby improve the purity of the recovered acrylic acid.

Other objects and effects of the present invention will be apparent from the following description.

The present inventors have made intensive studies for reducing the inclusion of acrolein in the recovered acrylic acid. As a result, it has been found that the hydration reaction of acrolein proceeds more as the temperature becomes higher, the acrolein concentration higher, and the condensate residence time longer. It has also been found that the formation of acrolein hydrate can therefore be inhibited by heightening the temperature of the condensing part to attain a lower acrolein concentration, by lowering the temperature of the condensate, and by reducing the condensate residence time as much as possible. The present invention has been completed based on the above findings.

The present invention relates to a process for producing acrolein which comprises bringing a reaction gas resulting from a catalytic oxidation of propylene into contact in a cooling tower with a condensate which is being circulated through the cooling tower and a circulating part, thereby to cool and separate the reaction gas and discharge an effluent gas from the cooling tower, the condensate in a bottom part of the cooling tower having a temperature of from 35° to 50° C., the effluent gas discharged from the cooling tower having a temperature of from 35° to 55° C., the temperature of the effluent gas being kept nearly equal to or higher than the temperature of the condensate in the bottom part of the cooling tower.

The present invention also relates to a process for producing acrolein which comprises bringing a reaction gas resulting from the catalytic oxidation of propylene into contact in a cooling tower with a condensate which is being circulated through the cooling tower and a circulating part, thereby to cool and separate the reaction gases, the period of the residence time of the condensate in the cooling tower and the circulating part being from 0.5 to 3 hours.

DETAILED DESCRIPTION OF THE INVENTION

Figure 1:
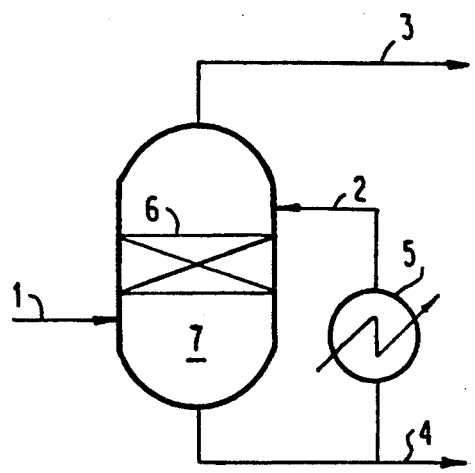
FIG. 1 is a schematic view illustrating a prior art method for cooling a reaction gas.

The catalytic oxidation reaction of propylene is usually conducted using an Mo-Bi catalyst at a temperature of about from 200° to 400° C. and a pressure of about from 1 to 1.5 Kg/cm$^2$G, with the propylene/air/steam molar ratio being 1/(7-9)/(3-4). The resulting reaction gas contains acrolein, acrylic acid, unreacted raw materials and others.

The reaction gas is generally cooled to about 35° to 55° C. in a cooling tower such as a packed tower, a perforated-plate tower and the like. The effluent gas containing non-condensed acrolein, nitrogen gas, and unreacted raw materials are introduced into an absorbing tower, where the acrolein is absorbed in water and separated from the other gases. The acrolein is then stripped from its aqueous solution and recovered.

The acrolein contained in the condensate is stripped at from 60° to 80° C. The thus-stripped acrolein is treated along with the above-mentioned effluent gas which is not condensed in the cooling tower. Acrylic acid is extracted from the resulting condensate with a solvent. The extracted acrylic acid is then recovered through separation by distillation.

In the present invention, the temperature of the condensate in the bottom part of the cooling tower is about from 35° to 50° C., preferably about from 40° to 45° C. and the temperature of the effluent gas discharged from the cooling tower is about from 35° to 55° C., preferably about from 40° to 45° C. with the effluent gas temperature being kept nearly equal to or higher than the temperature of the condensate in the bottom part of the tower. The temperature difference between the effluent gas and the condensate in the tower bottom part is maintained preferably in the range of about from −2°

C. to +20° C., more preferably about from 0° C. to +10° C. According to this method, the concentration of acrolein dissolved in the condensate can be lowered by regulating the gas condensation temperature at a value higher than conventional ones, and the rate of acrolein hydrate formation can be lessened by lowering the temperature of the condensate.

For attaining the above-described temperature control, a method can be used in which part of the condensate to be circulated is cooled and circulated to the bottom part and top part of the cooling tower, while the balance of the condensate is circulated to the top part of the tower without being cooled. The condensate is partly sent from the circulating line to the succeeding step of condensate treatment, in an amount corresponding to that newly condensed in the cooling tower.

The amount of acrolein hydrate formed increases substantially in proportion to the residence time of the acrolein in the aqueous layer. It is therefore preferred that in order to reduce the residence time as much as possible, the capacity of the condensate reservoir at the bottom part of the cooling tower is made smallest so long as stable operation in the cooling tower is possible.

The condensate-circulating part is also preferably constructed to have the smallest possible capacity. It is preferred that the condensate cooler to be installed in the circulating part is of a small capacity type such as the plate or spiral type or the like. While the period of the residence time of the condensate in the cooling tower and the circulating part has conventionally received little attention and been about from 4 to 7 hours, it preferably is reduced to the range of about from 0.5 to 3 hours, more preferably about from 0.5 to 1.5 hours.

The techniques described above are explained with reference to the figures. FIG. 1 illustrates a conventional method in which high-temperature reaction gases are fed from feading line 1, while a condensate is cooled with heat exchanger 5 and is then returned through circulating line 2 to the top part of the tower, where the reaction gas is cooled by being in contact with the condensate. In this case, the tower-top gas temperature is usually lower than the temperature of the tower-bottom condensate and, hence, condensation of acrolein is apt to occur in packed part 6. Moreover, since tower bottom part 7 has a high temperature, the hydration reaction of the condensed acrolein is apt to proceed. In FIG. 1, numeral 3 denotes a discharge line for cooled reaction gas, and numeral 4 denotes a discharge line of the condensate.

Figure 2:
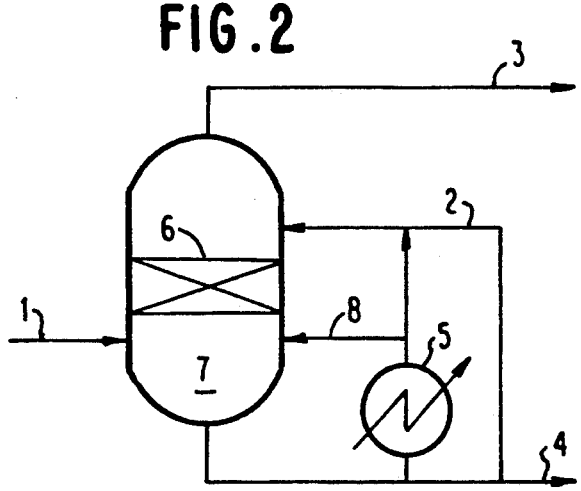
FIG. 2 is a schematic view illustrating one embodiment of the method for cooling a reaction gas according to the present invention.

FIG. 2, illustrates on embodiment of a method according to the present invention, in which part of a condensate is cooled with heat exchanger 5 and is then returned to a tower bottom part through line 8. Cooling of reaction gases is conducted by circulating a condensate having a higher temperature than conventional one, with which the cooled condensate has been partly mixed. In this case, the tower top temperature becomes relatively high, while the tower bottom temperature relatively low. As a result, the amount of acrolein that dissolves in the condensate decreases and, at the same time, the hydration reaction becomes less apt to proceed in the tower bottom part. It is desirable that the capacity of the tower bottom part and circulating part be made small as much as possible. Other numerals than described above, have the same meaning as in FIG. 1.

According to the process of the present invention, not only the formation of acrolein hydrate in the condensate can be inhibited thereby to reduce acrolein loss, but also high-purity acrylic acid can be recovered easily.

The present invention will be explained below in more detail with reference to the following examples, but the invention is not construed as being limited thereto.

EXAMPLE 1

Propylene was oxidized at ordinary pressure using an Mo-Bi catalyst to obtain a reaction gas having the composition as shown in Table 1. The gas was cooled by the method illustrated in FIG. 2. A packed tower having a diameter of 1.9 m and a height of 1.5 m was used as the cooling tower, which employed 2-inch stainless-steel pall rings as a packing material. A shell-and-tube heat exchanger having a heat transfer area of 135 $m^2$ was used as the cooler. The temperature conditions used and the results obtained are shown in Table 2. The residence time of the condensate in the cooling tower and the circulating part was 4.9 hours.

COMPARATIVE EXAMPLE 1

Cooling of the reaction gas was conducted by the method illustrated in FIG. 1, using the same packed tower and cooler as those employed in Example 1. The temperature conditions used and the results obtained are shown in Table 2. The residence time of the condensate in the cooling tower and the circulating part was 4.9 hours.

TABLE 1

| Component | Concentration (% by weight) |
|---|---|
| Nitrogen | 49.2 |
| Oxygen | 4.9 |
| Carbon dioxide | 1.6 |
| Propylene | 1.2 |
| Acrolein | 12.0 |
| Acrylic acid | 1.0 |
| Water | 27.3 |
| Others | 2.8 |

TABLE 2

|  | Example 1 | Comparative Example 1 |
|---|---|---|
| Temperature |  |  |
| Inlet gas (°C.) | 240–300 | 240–300 |
| Tower-top gas (°C.) | 39–42 | 39–41 |
| Tower-bottom liquid (°C.) | 39–42 | 48–52 |
| Condensate |  |  |
| Acrolein (% by weight) | 2.6–3.0 | 3.3–3.7 |
| Acrolein hydrate (% by weight) | 0.2–0.4 | 0.7–1.0 |

EXAMPLE 2

In practicing the method illustrated in FIG. 2, a plate-type heat exchanger was used as the cooler, the capacity of the bottom part of the cooling tower and that of the circulating part were made smaller. The residence time of the condensate in the cooling tower and the circulating part was 1.0 hour. The condensate temperature at the tower bottom part and the gas temperature at the tower top part were regulated at 42° C. and 45° C., respectively. By this method, the acrolein hydrate concentration in the condensate was reduced to 0.05–0.17% by weight. While the invention has been described in detail and with reference to specific embodiments thereof, it will be apparent to one skilled in the art that various changes and modifications can be made therein without departing from the spirit and scope thereof.

What is claimed is:

1. A process for producing acrolein which comprises bringing a reaction gas resulting from a catalytic oxidation of propylene into contact in a cooling tower with a condensate which is being circulated through said cooling tower and a circulating part, thereby to cool and separate said reaction gas and discharge an effluent gas from said cooling tower, said condensate in a bottom part of said cooling tower having a temperature of from 35° to 50° C., said effluent gas discharged from said cooling tower having a temperature of from 35° to 55° C., the temperature of said effluent gas being kept nearly equal to or higher than the temperature of said condensate in said bottom part of said cooling tower.

2. A process as claimed in claim 1, wherein part of said condensate to be circulated is cooled and circulated to said bottom part of the tower and to a top part of the tower, while the balance of said condensate is circulated, without being cooled, to said top part of the tower for cooling said reaction gas.

3. A process as claimed in claim 1, wherein the temperature difference between said effluent gas and said condensate in said bottom part of the tower is from −2° C. to +20° C.

4. A process for producing acrolein which comprises bringing a reaction gas resulting from the catalytic oxidation of propylene into contact in a cooling tower with a condensate which is being circulated through said cooling tower and a circulating part, thereby to cool and separate said reaction gases, the period of the residence time of said condensate in said cooling tower and said circulating part being from 0.5 to 3 hours.

5. A process as claimed in claim 1, wherein the period of the residence time of said condensate in said cooling tower and said circulating part is from 0.5 to 3 hours.

* * * * *